United States Patent
Hedrén et al.

(10) Patent No.: US 10,869,818 B2
(45) Date of Patent: Dec. 22, 2020

(54) FOAMABLE SKIN COMPOSITION

(71) Applicant: Paragon Nordic AB, Vallentuna (SE)

(72) Inventors: Marie Hedrén, Vallentuna (SE); Malin Burstedt, Vallentuna (SE)

(73) Assignee: PARAGON NORDIC AB, Vallentuna (SE)

(*) Notice: Subject to any disclaimer, the term of this patent is extended or adjusted under 35 U.S.C. 154(b) by 0 days.

(21) Appl. No.: 16/185,535

(22) Filed: Nov. 9, 2018

(65) Prior Publication Data

US 2019/0142710 A1    May 16, 2019

(30) Foreign Application Priority Data

Nov. 10, 2017 (SE) ................................. 1751397

(51) Int. Cl.
| | |
|---|---|
| A61K 8/04 | (2006.01) |
| A61Q 19/00 | (2006.01) |
| A61K 8/37 | (2006.01) |
| A61K 8/34 | (2006.01) |
| A61K 8/31 | (2006.01) |
| A61K 8/36 | (2006.01) |
| A61K 8/06 | (2006.01) |
| A61K 8/49 | (2006.01) |
| A61K 8/39 | (2006.01) |

(52) U.S. Cl.
CPC .............. *A61K 8/046* (2013.01); *A61K 8/062* (2013.01); *A61K 8/31* (2013.01); *A61K 8/342* (2013.01); *A61K 8/361* (2013.01); *A61K 8/37* (2013.01); *A61K 8/375* (2013.01); *A61K 8/39* (2013.01); *A61K 8/4973* (2013.01); *A61Q 19/00* (2013.01)

(58) Field of Classification Search
None
See application file for complete search history.

(56) References Cited

U.S. PATENT DOCUMENTS

| 4,808,388 A | 2/1989 | Beutler et al. |
|---|---|---|
| 5,993,830 A | 11/1999 | Freij |
| 2002/0182234 A1* | 12/2002 | Riedel ............... A61K 8/046 424/401 |

(Continued)

FOREIGN PATENT DOCUMENTS

| DE | 102009028156 A1 | 2/2011 |
|---|---|---|
| EP | 2494959 B1 | 11/2014 |

(Continued)

OTHER PUBLICATIONS

Dowsil 2501 (Cosmetic Wax Technical Date sheet, accessed Dec. 14, 2019). (Year: 2019).*

(Continued)

*Primary Examiner* — Melissa S Mercier
(74) *Attorney, Agent, or Firm* — Porter Wright Morris & Arthur LLP

(57) ABSTRACT

A foamable skin composition comprises, in % by weight of the foamable skin composition, at least one C12-C22 fatty acid at a concentration of 1-3%, at least one C12-C22 fatty alcohol at a concentration of 1-5%, at least one ester and/or vegetable oil at a concentration of 1-40%, at least one non-ionic surfactant at a concentration of 1-15%, at least one emollient at a concentration of 0.5-10% and water. The foamable skin composition has an acidic pH but still forms a stable form following dispensing.

23 Claims, 2 Drawing Sheets

(56) References Cited

U.S. PATENT DOCUMENTS

| | | |
|---|---|---|
| 2004/0202618 A1 | 10/2004 | Riedel et al. |
| 2006/0193789 A1* | 8/2006 | Tamarkin ............... A61K 8/046 |
| | | 424/47 |
| 2007/0098947 A1 | 5/2007 | Mueller |
| 2010/0092400 A1 | 4/2010 | Silvander et al. |
| 2012/0308492 A1 | 12/2012 | Allef et al. |
| 2017/0049700 A1 | 2/2017 | Siilvander et al. |
| 2017/0172877 A1 | 6/2017 | Buge et al. |

FOREIGN PATENT DOCUMENTS

| | | |
|---|---|---|
| WO | 03/007894 A2 | 1/2003 |
| WO | 2017/191532 A1 | 11/2017 |

OTHER PUBLICATIONS

Stearic Acid, Chemical Book, CAS DataBase List, accessed Dec. 14, 2019. (Year: 2019).*

Stearyl Alcohol, (TGSC Information Sheet, accessed Dec. 14, 2019). (Year: 2019).*

\* cited by examiner

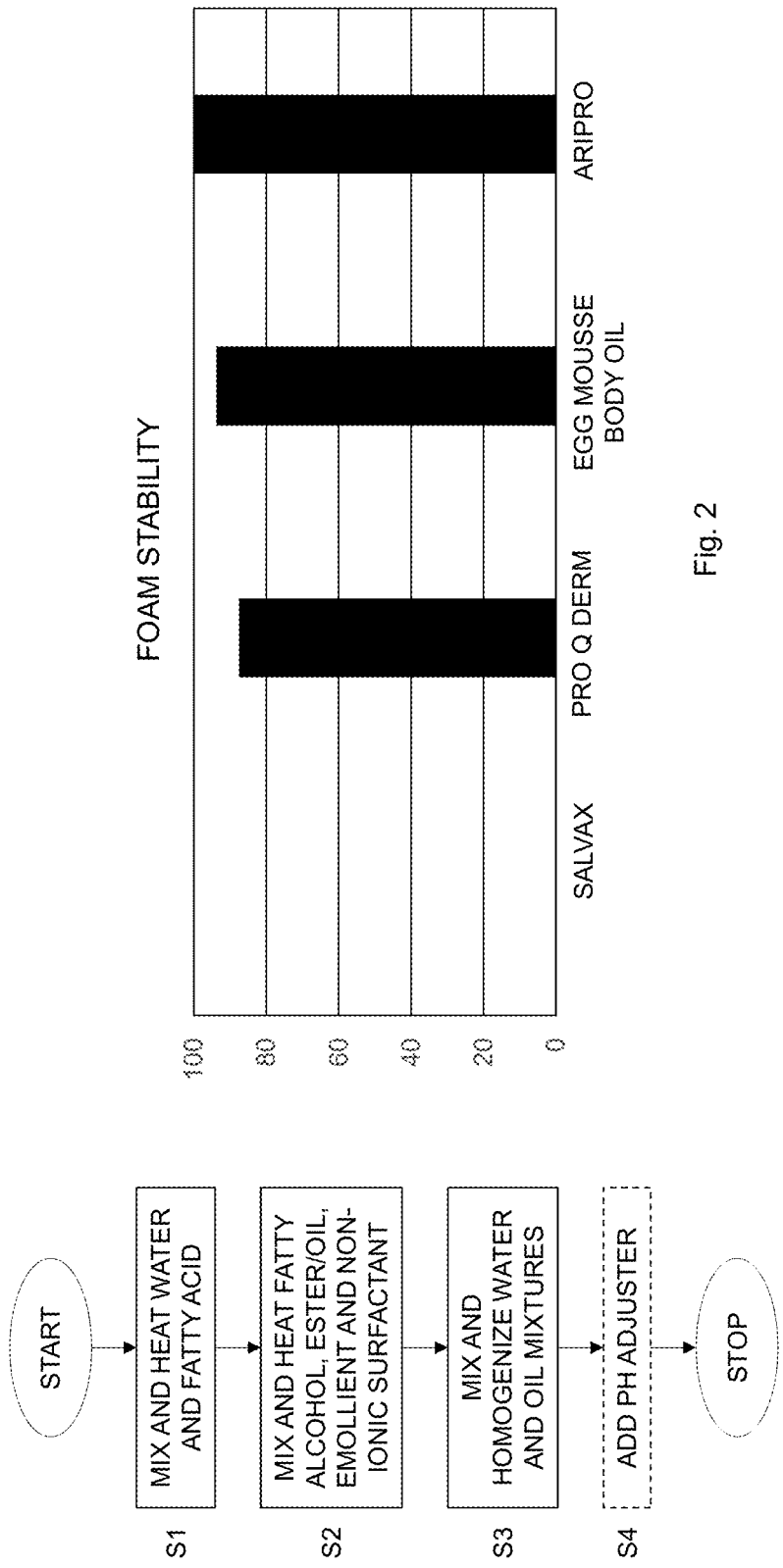

FOAMABLE SKIN COMPOSITION

TECHNICAL FIELD

The present invention generally relates to foamable skin compositions, and in particular to such foamable skin compositions having an acidic pH.

BACKGROUND

Foamable skin compositions are generally complicated systems with varying properties, such as foam stability. Stable foams are available on the market for various pharmaceutical or cosmetic applications. Such stable foams are, however, most often characterized by an alkaline or basic pH, i.e., a pH above 7.0 and most often above 7.5 or even above 8.0. This high pH has been a requisite in order to achieve sufficient foam stability.

The alkaline pH of foamable skin compositions forming stable foams is, however, much higher than the natural pH of the skin, which ranges from 4.5 to 6.5 but is most often below 5. This means that the pH of such stable foams is significantly higher than the physiologic pH of the human skin, which is generally undesirable.

The acidity of the skin is generally denoted "acid mantle" and is maintained by sebaceous glands, sweat glands, normal skin flora, among others. The acid mantle provides many protective functions to the skin. Application of a foamable skin composition with an alkaline pH may disrupt the stratum corneum, i.e., the uppermost layer of the skin, thereby damaging the barrier function of the skin, which translates into skin dryness and decreased antibacterial defense. For instance, usage of alkaline skin cleansers can cause this kind of damage even after one use, and the effect is cumulative, meaning it gets worse with repeated use (*International Journal of Dermatology* 2002; 41(8): 494-499).

Furthermore, foamable skin compositions may include active ingredients that lower the pH of composition to acidic pH ranges. Foamable skin compositions with an acidic pH, such as due to inclusion of acidic active ingredients, often suffer from low foam stability since the low pH destabilizes the foam after dispensing.

There is therefore a need for a foamable skin composition producing stable foams following dispensing while still having an acidic pH.

U.S. Pat. No. 5,993,830 discloses a skin preparation comprising lipohilic and hydrophilic components. The skin preparation exists as a two-phase system and is capable of creating a semi-permeable membrane in the skin.

U.S. patent application no. 2017/0049700 discloses an aerosol delivery system for a water-based salicylic acid composition comprising salicylic acid, lipohilic component (s) and a frothing agent. The salicylic acid composition has a low viscosity to support aerosol delivery and forms a foam upon propellant-driven aerosol delivery.

SUMMARY

It is a general objective to provide a foamable skin composition having an acidic pH and producing stable foams following dispensing.

This and other objectives are met by embodiments as disclosed herein.

The present invention relates to a foamable skin composition and a method of producing a foamable skin composition as defined in the independent claims.

Further embodiments of the present invention are defined in the amended claims.

A foamable skin composition according to the present invention comprises, in % by weight of the foamable skin composition, at least one C12-C22 fatty acid at a concentration of 1-3%, at least one C12-C22 fatty alcohol at a concentration of 1-5%, at least one ester and/or vegetable oil at a concentration of 1-40%, at least one non-ionic surfactant at a concentration of 1-15%, at least one emollient at a concentration of 0.5-10% and water. The foamable skin composition has an acidic pH but still forms a stable form following dispensing.

BRIEF DESCRIPTION OF THE DRAWINGS

The embodiments, together with further objects and advantages thereof, may best be understood by making reference to the following description taken together with the accompanying drawings, in which:

FIG. 1 is a flow chart illustrating a method of producing a foamable skin composition according to an embodiment;

FIG. 2 is a diagram comparing foam stability of three prior art foams and a foam according to the invention;

DETAILED DESCRIPTION

Figure 4:
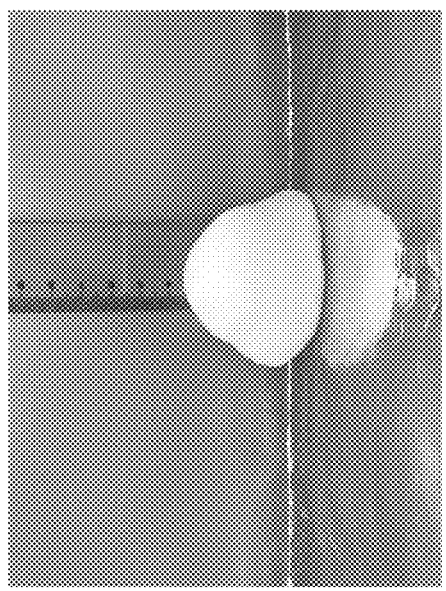
FIG. 4 is a photograph of a foam according to the invention 1 min after dispensing.

The present invention generally relates to foamable skin compositions, and in particular to such foamable skin compositions having an acidic pH.

The foamable skin composition of the invention achieves a stable foam after dispensing despite having an acidic pH. This means that the foamable skin composition according to the invention can be used as a skin friendly composition to be applied to the skin for various pharmaceutical and/or cosmetic uses where there is a general need to have an acidic pH. For instance, the foamable skin composition could be formulated to have a pH within the physiologic range of the human or animal skin, such as within about 4.5 to about 6.5, and generally below 5.0. The foamable skin composition could also be used as a carrier for active ingredients or agents having an acidic pH, and thereby contributing to an acidic pH of the foamable skin composition when included in the composition.

The foam stability of the foamable skin composition of the present embodiments significantly simplifies application of the composition to the skin in terms of usability and compliance. Furthermore, the stable foam of the foamable skin composition improves spreadability of the composition on the skin and also achieves a cosmetic elegance.

The foamable skin composition also has a low viscosity, which further simplifies application of the composition to the skin. The composition is furthermore easy to fill in a production line. Another advantage of the foamable skin composition of the invention is that it provides a rich foamable texture.

An aspect of the invention relates to a foamable skin composition. The composition comprises at least one C12-C22 fatty acid at a concentration of 1-3% and at least one C12-C22 fatty alcohol at a concentration of 1-5%. The composition also comprises at least one ester and/or vegetable oil at a concentration of 1-40%. The composition further comprises at least one non-ionic surfactant at a concentration of 1-15% and at least one emollient at a concentration of 0.5-5%. The above mentioned concentrations are in % by weight of the foamable skin composition. The composition also comprises water and has an acidic pH.

Herein, reference to an ingredient at a concentration of X-Y % by weight of the foamable skin composition implies that the ingredient is present in the foamable skin composition at a concentration within an interval of from, and including, X % by weight of the foamable skin composition up to, and including, Y % by weight of the foamable skin composition.

In an embodiment, the foamable skin composition also comprises at least one propellant. The at least one propellant is thereby used to dispense the foamable skin composition as a foam or mousse.

Any propellant or mixture of propellants used in the art of dispensing foamable skin compositions can be used according to the embodiments.

In an embodiment, the at least one propellant is preferably selected from the group consisting of liquefied petroleum gas, butane, propane, isobutane and a mixture thereof. In a particular embodiment, the at least one propellant is selected from the group consisting of propane, butane, isobutane, and a mixture thereof, and is preferably a mixture of propane, butane and isobutane.

The concentrations of ingredients of the foamable skin compositions are in % by weight of the foamable skin composition excluding any propellant.

The at least one C12-C22 fatty acid could be at least one fatty acid having an aliphatic chain of from 12 up to 22 carbon atoms. The at least one C12-C22 fatty acid could alternatively be in the form of a mixture of multiple, i.e., at least two, C12-C22 fatty acids. The at least one C12-C22 fatty acid could be at least one saturated C12-C22 fatty acid, at least one unsaturated C12-C22 fatty acid or a mixture of at least one saturated C12-C22 fatty acid and at least one unsaturated C12-C22 fatty acid.

The at least one C12-C22 fatty acid stabilizes the foamable skin composition and gives it a more rich feeling. Moreover, the at least one C12-C22 fatty acid is skin conditioning, which is advantageous for dry and/or sensitive skin.

In an embodiment, the at least one C12-C22 fatty acid is selected from the group consisting of lauric acid (12:0), tridecylic acid (13:0), myristic acid (14:0), myristoleic acid (cis-$\Delta$9, 14:1), pentadecylic acid (15:0), palmitic acid (16:0), palmitoleic acid (cis-$\Delta$9, 16:1), sapienic acid (cis-$\Delta$6, 16:1), margaric acid (17:0), stearic acid (18:0), oleic acid (cis-$\Delta$9, 18:1), elaidic acid (trans-$\Delta$9, 18:1), vaccenic acid (trans-All, 18:1), linoleic acid (cis,cis-$\Delta$9,$\Delta$12, 18:2), linoelaidic acid (trans,trans-$\Delta$9,$\Delta$12, 18:2), $\alpha$-linolenic acid (cis,cis,cis-$\Delta$9, $\Delta$12,$\Delta$15, 18:3), $\gamma$-linolenic acid (cis,cis,cis-$\Delta$6,$\Delta$9,$\Delta$12, 18:3), pinolenic acid (cis,cis,cis-$\Delta$5,$\Delta$9,$\Delta$12, 18:3), $\alpha$-elostearic acid (cis,trans,trans-$\Delta$9,$\Delta$11,$\Delta$13, 18:3), $\beta$-elostearic acid (trans,trans,trans-$\Delta$9,$\Delta$11,$\Delta$13, 18:3), stearidonic acid (cis,cis,cis,cis-$\Delta$6,$\Delta$9,$\Delta$12,$\Delta$15, 18:4), bosseopentaenoic acid (cis,cis,trans,trans,cis-$\Delta$5,$\Delta$8,$\Delta$10,$\Delta$12,$\Delta$14, C18:5), nonadecylic acid (19:0), arachidic acid (20:0), paullinic acid (cis-$\Delta$13, 20:1), eicosenoic acid (cis-$\Delta$11, 20:1), gadoleic acid (cis-$\Delta$9, 20:1), eicosadienoic acid (cis,cis-$\Delta$11, $\Delta$14, 20:2), mead acid (cis,cis,cis-$\Delta$5,$\Delta$8,$\Delta$11, 20:3), dihomo-$\gamma$-linolenic acid (cis,cis,cis-$\Delta$8,$\Delta$11,$\Delta$14, 20:3), eicosatrienoic acid (cis,cis,cis-$\Delta$11,$\Delta$14,$\Delta$17, 20:3) arachidonic acid (cis, cis,cis,cis-$\Delta$5,$\Delta$8,$\Delta$11,$\Delta$14, 20:4), eicosatetraenoic acid (cis, cis,cis,cis-$\Delta$8,$\Delta$11,$\Delta$14,$\Delta$17, 20:4), eicosapentaenoic acid (cis,cis,cis,cis,cis-$\Delta$5,$\Delta$8,$\Delta$11,$\Delta$14,$\Delta$17, 20:5), heneicosylic acid (21:0), behenic acid (22:0), erucic acid (cis-$\Delta$13, 22:1), docosadienoic acid (cis,cis-$\Delta$13,$\Delta$16, 22:2), docosatetraenoic acid (cis,cis,cis,cis-$\Delta$7,$\Delta$10,$\Delta$13,$\Delta$16, 22:4), ozubondo acid (cis,cis,cis,cis,cis-$\Delta$4,$\Delta$7,$\Delta$10,$\Delta$13,$\Delta$16, 22:5), sardine acid (cis,cis,cis,cis,cis-$\Delta$7,$\Delta$10,$\Delta$13,$\Delta$16,$\Delta$19, 22:5), docosahexaenoic acid (cis,cis,cis,cis,cis,cis-$\Delta$4,$\Delta$7,$\Delta$10,$\Delta$13,$\Delta$16, $\Delta$19, 22:6), and a mixture thereof.

Generally, fatty acids having a shorter aliphatic chain than C12 have a too low viscosity at room temperature to provide a stabilizing effect to the foamable skin composition. Correspondingly, fatty acids having an aliphatic chain longer than C22 have a too high viscosity and thereby result in a foamable skin composition with too high viscosity.

In an embodiment, the at least one C12-C22 fatty acid is at least one C12-C18 fatty acid.

In an embodiment, the at least one C12-C18 fatty acid is selected from the group consisting of lauric acid, tridecylic acid, myristic acid, myristoleic acid, pentadecylic acid, palmitic acid, palmitoleic acid, sapienic acid, margaric acid, stearic acid, oleic acid, elaidic acid, vaccenic acid, linoleic acid, linoelaidic acid, $\alpha$-linolenic acid, $\gamma$-linolenic acid, pinolenic acid, $\alpha$-elostearic acid, $\beta$-elostearic acid, stearidonic acid, bosseopentaenoic acid, and a mixture thereof.

In a particular embodiment, the at least one C12-C18 fatty acid is selected from the group consisting of myristic acid, myristoleic acid, palmitic acid, palmitoleic acid, sapienic acid, stearic acid, oleic acid, elaidic acid, vaccenic acid, linoleic acid, linoelaidic acid and a mixture thereof.

The at least one C12-C18 fatty acid is more preferably selected from the group consisting of stearic acid, palmitic acid and a mixture thereof. The at least one C12-C18 fatty acid is preferably a mixture of stearic acid and palmitic acid, such as a 1:1 mixture of stearic acid and palmitic acid.

In an embodiment, the at least one C12-C22 fatty acid is at a concentration of 1.25-2.75% by weight of the foamable skin composition, preferably at a concentration of 1.5-2.5% by weight, and more preferably at a concentration of 1.75-2.25% by weight. In a particular embodiment, the at least one C12-C22 fatty acid is at a concentration of about 2% by weight of the foamable skin composition.

With a too low concentration of the at least one C12-C22 fatty acid, i.e., lower than 1.25% by weight, the foamable skin composition will not be sufficiently stabilized. Correspondingly, a too high concentration, i.e., above 2.75% by weight, will give the foamable skin composition a high pH, which cannot be adjusted without breaking the emulsion stability. Hence, C12-C22 fatty acids included in the foamable skin composition will increase the pH of the foamable skin composition.

The at least one C12-C22 fatty alcohol could be at least one fatty alcohol having an aliphatic chain of from 12 up to 22 carbon atoms. The at least one C12-C22 fatty alcohol could alternatively be in the form of a mixture of multiple C12-C22 fatty alcohols.

The at least one C12-C22 fatty alcohol is foam boosting and emulsion stabilizing and provides a fuller and richer foam when applying the foamble skin composition. Moreover, the at least one C12-C22 fatty alcohol work as emollient, which is advantageous for dry skin.

In an embodiment, the at least one C12-C22 fatty alcohol is selected from the group consisting of lauryl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, heneicosyl alcohol, behenyl alcohol, erucyl alcohol, cetearyl alcohol, and a mixture thereof.

C12-C22 fatty alcohols have foam boosting and emulsion stabilizing effect without having too high viscosity. Shorter chain fatty alcohols generally do not have sufficient foam boosting and emulsion stabilizing effect, whereas longer chain fatty alcohols will negatively increase the viscosity of the foamable skin composition.

In an embodiment, the at least one C12-C22 fatty alcohol is a C12-C18 fatty alcohol.

In an embodiment, the C12-C18 fatty alcohol is selected from the group consisting of lauryl alcohol, myristyl alcohol, pentadecyl alcohol, cetyl alcohol, palmitoleyl alcohol, heptadecyl alcohol, stearyl alcohol, oleyl alcohol, cetearyl alcohol and a mixture thereof.

In a particular embodiment, the C12-C18 fatty alcohol is selected from the group consisting of myristyl alcohol, cetyl alcohol, stearyl alcohol, cetearyl alcohol, and a mixture thereof.

In a preferred embodiment, the C12-C18 fatty alcohol is cetearyl alcohol. Cetearyl alcohol, also referred to as cetostearyl alcohol or cetylstearyl alcohol, is a mixture of fatty alcohols, consisting predominantly of cetyl and stearyl alcohols.

In an embodiment, the at least one C12-C22 fatty alcohol is at a concentration of 1-4.5% by weight of the foamable skin composition, preferably at a concentration of 1-4% by weight, such as at a concentration of 1-3% by weight, at a concentration of 1.25-2.75% by weight or at a concentration of 1.5-2.5% by weight, and more preferably at a concentration of 1.75-2.25% by weight. In a particular embodiment, the at least one C12-C22 fatty alcohol is at a concentration of about 2% by weight of the foamable skin composition.

The foamable skin composition preferably comprises at least 1% by weight of the C12-C22 fatty alcohol to provide sufficient foam boosting and emulsion stabilization. Too high concentration of the C12-C22 fatty alcohol, i.e., above 4.5% by weight will give a too high viscosity to the foamable skin composition.

The foamable skin composition comprises at least one non-ionic surfactant. The composition could comprise a single such non-ionic surfactant or a mixture of multiple non-ionic surfactants.

The at least one non-ionic surfactant is included in the foamable skin composition to facilitate mixing of water and oil components to an emulsion. In addition, the at least one non-ionic surfactant is a mild surfactant to the skin.

Generally, the at least one non-ionic surfactant could be selected among such non-ionic surfactants commonly used in foamable skin compositions. In an embodiment, the at least one non-ionic surfactant is selected from the group consisting of esters of fatty acids and polyols, polyglyceryl fatty acid esters, ethoxylated sorbitan esterified with fatty acids, and a mixture thereof.

In a particular embodiment, the at least one non-ionic surfactant is selected from the group consisting of sorbitan laurate, polyglycerol-4 laurate, polyglycerol-4 succinate, polysorbate and a mixture thereof.

Sorbitan laurate is a mixture of esters formed from the fatty acid lauric acid (C12:0) and polyols derived from sorbitol, including sorbitan and isosorbide. Polyglycerol-4 laurate is an ester of lauric acid and polygylcerin-4. Correspondingly, polyglycerol-4 succinate is an ester of succinic acid and polyglycerin-4. Polysorbates are oily liquids derived from ethoxylated sorbitan esterified with fatty acids. The polysorbate is preferably selected from the group consisting of polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), and a mixture thereof.

The at least one non-ionic surfactant is preferably selected from the group consisting of sorbitan laurate, polyglycerol-4 laurate, polyglycerol-4 succinate and a mixture thereof. The non-ionic surfactant is more preferably a mixture of sorbitan laurate, polyglycerol-4 laurate and polyglycerol-4 succinate.

In an embodiment, the at least one non-ionic surfactant is at a concentration of 1-10% by weight of the foamable skin composition, such as at a concentration of 2-8% by weight, at a concentration of 3-7% by weight, and more preferably at a concentration of 4-6% by weight of the foamable skin composition. In a particular embodiment, the at least one non-ionic surfactant is at a concentration of about 4.9% by weight of the foamable skin composition. For instance, the foamable skin composition preferably comprises about 2% by weight of sorbitan laurate and about 2.9% by weight of polyglycerol-4 laurate/succinate.

Generally, at least 1% by weight of the non-ionic surfactant should be included in the foamable skin composition to achieve a stable emulsion. Too high amounts of the non-ionic surfactant, i.e., above 10% by weight, results in an unstable foam and a sticky feeling on the skin.

The foamable skin composition comprises at least one ester and/or at least one vegetable oil. The composition could comprise a single such ester, a mixture of multiple esters, a single vegetable oil, a mixture of multiple vegetable oils, a mixture of one ester and one vegetable oil, a mixture of multiple esters and one vegetable oil, a mixture of one ester and multiple vegetable oils or a mixture of multiple esters and multiple vegetable oils.

The at least one ester and/or the vegetable oil is included in the foamable skin composition for a nice and soft skin feeling. The at least one ester and/or vegetable oil may also have various effects to the foamable skin composition including, for instance, skin emollient, humectant, soothing, increasing emulsion stability and being skin protective.

The ester and/or vegetable oil can be selected among such esters and vegetable oils used in foamable skin compositions.

In an embodiment, the at least one ester and/or vegetable oil is at least one ester selected from the group consisting of at least one medium chain triglyceride, diisopropyl adipate, butylene glycol dicaprylate, butylene glycol dicaprate, and a mixture thereof.

The at least one medium chain triglyceride (MCT) is preferably at least one triglyceride, the fatty acids of which have an aliphatic tail or chain of 6 to 12 carbon atoms. In an embodiment, the at least one medium chain triglyceride is selected from the group consisting of caprylic triglyceride, capric triglyceride, and a mixture thereof. In an embodiment, the at least one medium chain triglyceride is preferably a mixture of caprylic triglyceride and capric triglyceride.

In a particular embodiment, the at least one ester is a mixture of caprylic triglyceride, capric triglyceride, diisopropyl adipate, butylene glycol dicaprylate and butylene glycol dicaprate.

The vegetable oil or oil mixture is preferably selected from a group consisting of sesame oil, olive oil, almond oil, apricot kernel oil, avocado oil, evening primerose oil, grapeseed oil, hazelnut oil, jojoba oil, pumpkiness oil, roseship oil, safflower oil, walnut oil, wheatgerm oil, sunflower oil, and a mixture thereof.

In a particular embodiment, the vegetable oil or oil mixture is selected from the group consisting of sesame oil, olive oil, and a mixture thereof, and is preferably olive oil.

In an embodiment, the at least one ester and/or vegetable oil is at a concentration of 1-30% by weight of the foamable skin composition, preferably at a concentration of 1-20% by weight, such as at a concentration of 2.5-15% by weight, and more preferably at a concentration of 5-10% by weight of the foamable skin composition. In a particular embodiment, the at least one ester and/or vegetable oil is at a concentration of about 7% by weight of the foamable skin composition. For instance, the foamable skin composition preferably comprises about 2.5% by weight of caprylic/capric triglyceride, about 2.5% by weight of diisopropyl adipate, and about 2% by weight of butylene glycol dicaprylate/dicaprate.

Generally, at least 1% by weight of the at least one ester and/or vegetable oil is needed to adjust the skin feeling of the foamable skin composition. A concentration above 30% by weight of the at least one ester and/or vegetable oil may cause separation of the emulsion, and also of the foam formed following application of the foamable skin composition.

The foamable skin composition comprises at least one emollient. The composition could comprise a single such emollient or a mixture of multiple emollients.

The at least one emollient gives a more rich body of the foamable skin composition and also acts as skin protectant and humectant for dry and/or sensitive skin.

Generally, the at least one emollient could be selected among such emollients commonly used in foamable skin compositions.

In an embodiment, the at least one emollient is selected from the group consisting of squalane, isodecyl neopentanoate, dimethicone, paraffinum liquidum, diethylhexyl maleate, diethylhexyl malate and a mixture thereof.

In a particular embodiment, the at least one emollient is squalane.

In an embodiment, the at least one emollient is at a concentration of 0.5-10% by weight of the foamable skin composition, preferably at a concentration of 1-8% by weight, such as at a concentration of 1.25-6% by weight or at a concentration of 1.5-5% by weight, and more preferably at a concentration of 1.5-2.5% by weight, such as about 2% by weight of the foamable skin composition.

Generally, at least 0.5% by weight of the at least one emollient is needed in order to achieve a fuller foam body following application of the foamable skin composition. Too high concentration of the at least one emollient, i.e., above 10% by weight, will make the foam less stable.

In an embodiment, the foamable skin composition comprises at least one humectant at a concentration of 1-40% by weight of the foamable skin composition.

The foamable skin composition could comprise a single such humectant or a mixture of multiple humectants.

The at least one humectant is preferable added for dry skin conditions.

Generally, the at least one humectant could be selected among such humectants commonly used in foamable skin compositions.

In an embodiment, the at least one humectant is selected from the group consisting of a propanediol, such as 1,2-propanedioal, 1,3-propanediol and/or 2,2-propanediol; glycerol; urea; betaine and a mixture thereof.

In a particular embodiment, the at least one humectant is preferably a propanediol, and more preferably 1,3-propanediol, urea, and a mixture thereof.

In an embodiment, the at least one humectant is at a concentration of 1-30% by weight of the foamable skin composition, preferably at a concentration of 1-20% by weight, such as at a concentration of 1-15% by weight, and more preferably at a concentration of 2.5-10% by weight of the foamable skin composition. In a particular embodiment, the at least one humectant is at a concentration of about 5% by weight of the foamable skin composition.

In order to provide sufficient skin moisture, at least 1% humectant is preferably included in the foamable skin composition. Too much humectant, i.e., above 30% by weight, may, however, negatively affect the foam stability and skin feeling.

In an embodiment, the foamable skin composition comprises at least one pH adjuster at a concentration sufficient to achieve an acidic pH of the foamable skin composition.

In an embodiment, the at least one pH adjuster is at least one acid included to adjust the pH of the foamable skin composition to an acidic pH. The foamable skin composition could comprise a single such pH adjuster, such as acid, or a mixture of multiple pH adjusters, such as multiple acids.

Generally, the at least one acid could be selected among such acids commonly used in foamable skin compositions.

In an embodiment, the at least one pH adjuster is selected from the group consisting of lactic acid, citric acid, hydroiodic acid, acetic acid, hydrochloric acid and a mixture thereof.

In a particular embodiment, the at least one pH adjuster is lactic acid.

In some applications it may actually be desired to increase the pH of the foamable skin composition in order to get a target acidic pH. In such a case, an alkaline pH adjuster may be added, such as NaOH or KOH.

In an embodiment, the foamable skin composition has a pH within an interval of from 3 up to 6, more preferably within an interval of from 4 up to 5.5, such as about 4.4 or 4.5. Thus, in preferred embodiment, the at least one pH adjuster is at a concentration sufficient to achieve a pH of 3-6 of the foamable skin composition, preferably a pH of 4-5.5.

In an embodiment, the foamable skin composition comprises at least one pharmaceutically active agent. The foamable skin composition could comprise a single such pharmaceutically active agent or a mixture of multiple pharmaceutically active agents. In these embodiments, the foamable skin composition may function as a carrier to the at least one pharmaceutically active agent.

Non-limiting examples of pharmaceutically acceptable agents that can be used according to the embodiments include anti-inflammatory agents, anesthetic, analgesic, anti-viral agents, anti-bacterial agents, anti-irritant agents, vitamins, sun filters, and mixtures thereof.

Examples of anti-inflammatory agents include non-steroidal anti-inflammatory drugs (NSAIDs) including salicylates, such as aspirin, diflunisal, salsalate, choline magnesium trisalicylate; propionic acid derivates, such ibuprofen, dexibuprofen, naproxen, fenoprofen, ketoprofen, dexketoprofen, flurbiprofen, oxaprozin, loxoprofen; acetic acid derivatives, such as indomethacin, tolmetin, sulindac, etodolac, ketorolac, diclofenac, acelofenac, nabumetone; enolic acid derivatives, such as piroxicam, meloxicam, tenoxicam, droxicam, lornoxicam, isoxicam; anthranilic acid derivatives, such as mefenamic acid, meclofenamic acid, flufenamic acid, tolfenamic acid; selective COX-2 inhibitors, such as celecoxib, rofecoxib, valdecoxib, parecoxib, lumiracoxib, etoricoxib, firocoxib; sulfananilides, such as nimesulfide; licofelone; corticosteroids.

Examples of anti-viral agents include amantadine; rimantadine; pleconaril; acyclovir; zidovudine; lamivudine; rifampicin; zanamivir and oseltamivir.

Examples of anti-bacterial agents (sometimes also referred to as anti-septic agents) include bactericides, such as Daquin's solution, sodium benzenesulfochloramide, iodopovidone, urea perhydrate solutions, peracetic acid solutions, sorbic acid, benzoic acid, lactic acid, salicylic acid, hexachlorophene, triclosan, dibromol, benzalkonium, chlorhexidine, octenidine solutions, beta-lactam antibiotics, vancomycin, daptomycin, fluoroquinolones, metronidazole, nitrofurantoin, co-trimoxazole, telithromycin, aminoglycosidic antibiotics; and bacteriostatic agents, such as tetracyclines, sulfonamides, spectinomycin, trimethoprim, chloramphenicol, macrolides, lincosamides, clindamycin, ethambutol, nitrofurantoin, novobiocin, tigecycline, oxazolidinone.

Example of anti-irritant agents, also denoted soothing agents in the art, include allantoin, menthol, Aloe Vera, bisbolol, *Cucumis melo* juice, jojoba esters, methyl nicotinate, *Ononis spinosa* root extract, *Salvia officinalis* extract, naringenin, and d-panthenyltriacetate.

Examples of anesthetic agents include local anesthetic agents in particular ester anesthetics, such as procaine benzocaine, chloroprocaine, cyclomethycaine, dimethocaine/larocaine, piperocaine, propoxycaine, procaine/novocaine, proparacaine, tetracaine/amethocaine; and amide anesthetics, such as lidocaine articaine, bupivacaine, cinchocaine/dibucaine, etidocaine, levobupivacaine, lidocaine/lignocaine, mepivacaine, prilocaine, ropivacaine, trimecaine.

Examples of analgesic agents include paracetamol; NSAIDs; COX-2 inhibitors; opioids, such as morphine, codeine, oxycodone, hydrocodone, dihydromorphine, pethidine, buprenorphine tramadol, tapentadol; flupirtine; tricyclic antidepressants, such as amitriptyline; nefopam; carbamazepine; gabapentin; pregabalin.

In a particular embodiment, the pharmaceutically active agent is selected from a group consisting of a corticosteroid, oxymetazoline, phenylephrine, xylometazoline, naphazoline, eucalyptus, menthol, Aloe Vera, acrivastine, azelastin or a mixture thereof.

Further examples of pharmaceutically active agents include salicylic acid, allantoin and tocopherols.

Salicylic acid is a lipophilic monohydroxybenzoic acid, a type of phenolic acid, and a beta hydroxy acid (BHA). Salicylic acid as a medication is used most commonly to help remove the outer layer of the skin. As such it is used to treat warts, psoriasis, dandruff, acne, ringworm, and ichthyosis. As with other hydroxy acids, salicylic acid is a key ingredient in many skin-care products for the treatment of seborrhoeic dermatitis, acne, psoriasis, calluses, corns, xerosis, keratosis pilaris, keratosis plantaris, keratosis palmaris, acanthosis nigricans, ichthyosis and warts.

Allantoin, also referred to as 5-ureidohydantoin or glyoxyldiureide, is a diureide of glyoxylic acid. Allantoin may be included as an active agent to achieve a moisturizing and keratolytic effect, to increase the water content of the extracellular matrix, to enhance the desquamation of upper layers of dead skin cells, to increase the smoothness of the skin, to promote cell proliferation and wound healing, to achieve a soothing, anti-irritant, and skin protectant effect by forming complexes with irritant and sensitizing agents. Allantoin ameliorates the wound healing process, by modulating the inflammatory response. Allantoin also promotes fibroblast proliferation and synthesis of the extracellular matrix. Allantoin has also effect in treatment of pruritus in mild-to-moderate atopic dermatitis.

Tocopherols (TCP) are a class of methylated phenols having vitamin E activity. Tocopherols may be used in topical applications as an antioxidant. In such a case, the tocopherol may be in the form of tocopherol acetate, tocopheryl linoleate or tocopheryl nicotinate. Tocopherols as vitamin E source play a role in encouraging skin healing and reducing scarring after injuries, such as burns. Other vitamins can be vitamin C, vitamin B, vitamin D, vitamin K and vitamin A.

Examples of sun filters are both chemical and physical sun filters, such as octocrylene, diethylhexyl buramido triazone, butyl methoxydibenzoylmethane, diethylamino hydroxybenzoyl hexyl benzoate, bis-ethylhexyloxyphenol methoxyphenyl triazine, ethylhexyl triazone, zink oxide, titanium dioxide.

The foamable skin composition of the present invention can be formulated for various pharmacological or cosmetic applications or uses. The foamable skin composition is preferably formulated for human use, i.e., is to be applied to the skin of a human. The foamable skin composition may, however, also, or alternatively, be formulated for veterinary applications, i.e., be applied to the skin of an animal, preferably of a mammal. Non-limiting, but illustrative, examples of such mammals include mouse, rat, horse, cow, dog, cat, sheep, goat, rabbit, monkey, and ape.

The composition could be used to treat different dry skin conditions, redness, burns, acne, keratosis pilaris, dandruff, atopic dermatitis, eczema, psoriasis, rosacea, wounds, bedsores, heel cracks, skin inflammations, skin infections, as sun screen protectant, etc.

In some embodiment, the at least one active agent may affect the pH of the foamable skin composition and, in particular, reduce the pH of the composition. For instance, salicylic acid could be added as active agent to treat, prevent or at least inhibit hyperkeratotic skin disorders, such as ichthyoses, keratosis pilaris, keratosis palmaris, keratosis plantaris, psoriasis, and xerosis. The salicylic acid will then both act as an active agent and adjust the pH of the foamable skin composition.

The foamable skin composition of the present invention is able to provide a stable foam on the skin of subject. Such a stable foam should be in the form of a ball-like, non-porous, cosmetically elegant foam.

In an embodiment, the foamable skin composition has a foam stability of at least 50%. In an embodiment, the foam stability is at least 60%, preferably at least 70%, such as at least 75% or at least 80%. In some applications the foam stability may be even higher, such as at least 85% or even at least 90%.

Foam stability in % as used herein is obtained by $100-100\times(H_0-H_1)/H_0$, which is equivalent to $100\times H_1/H_0$, wherein $H_0$ represents the height of the foam directly after dispensing the foamable skin composition onto a surface, such as the skin, and $H_1$ represents the height of the foam 1 minute after dispensing.

In an embodiment, the foamable skin composition of the present invention has a foam density within an interval of from 20 mg/ml up to 60 mg/ml, preferably within an interval of from 25 mg/ml up to 50 mg/ml, and more preferably within an interval of from 25 mg/ml up to 40 mg/ml, such as within an interval of from 25 mg/ml up to 35 mg/ml.

A too high foam density, such as above 60 mg/ml, gives the foamable skin composition a non-foam feeling, more like a creamy feeling. A too low foam density, such as below 20 mg/ml, gives a too light non-ball-like foam.

In an embodiment, the foamable skin composition is not a foamable skin cleanser.

In a particular embodiment, the foamable skin composition comprises the following ingredients in % by weight of the foamable skin composition:
  a mixture of stearic acid and palmitic acid at a concentration of 1-3% by weight;
  cetearyl alcohol at a concentration of 1-5% by weight;

a mixture of caprylic triglyceride, capric triglyceride, diisopropyl adipate, bytelene glycol dicaprylate and butylene glycol dicaprate at a concentration of 1-40% by weight;

a mixture of sorbitan laurate, polyglycerol-4 laurate and polyglycerol-4 succinate at a concentration of 1-15% by weight;

squalene at a concentration of 0.5-5% by weight; and water.

In another particular embodiment, the foamable skin composition additionally comprises 1,3-propanediol at a concentration of 1-40% by weight.

In a further particular embodiment, the foamable skin composition comprises the following ingredients in % by weight of the foamable skin composition:

stearic acid and palmitic acid at a concentration of 2% by weight;
cetearyl alcohol at a concentration of 2% by weight;
diisopropyl adipate at a concentration of 2.5% by weight;
caprylic triglyceride and capric triglyceride at a concentration of 2.5% by weight;
butylene glycol dicaprylate and butylene glycol dicaprate at a concentration of 2% by weight; 1,3-propanediol at a concentration of 4 or 5% by weight;
sorbitan laurate at a concentration of 2% by weight;
polyglycerol-4 laurate and polyglycerol-4 succinate at a concentration of 2.9% by weight;
squalane at a concentration of 2% by weight; and water.

In a particular embodiment, the foamable skin composition comprises water at a concentration of 76.5% by weight.

The foamable skin composition may also comprise urea at a concentration of 10% by weight, or at a concentration of 25% by weight.

In another embodiment, the foamable skin composition may also comprise a sun filter or block, such as a sun protection factor (SPF) 50 sun filter or block.

The foamable skin composition according to any of the above presented particular embodiments may additionally comprise lactic acid at a concentration sufficient to achieve an acidic pH of the foamable skin composition.

The foamable skin composition according to any of the above presented particular embodiments may additionally comprise at least one pharmaceutically active agent, such as allantoin and/or tocopherol.

Another aspect of the embodiments relates to a method of producing a foamable skin composition as shown in FIG. 1. The method comprises mixing and heating, in step S1, water and at least one C12-C22 fatty acid at a concentration of 1-3% by weight of the foamable skin composition until the at least one C12-C22 fatty acid melts to form a water mixture. The method also comprises mixing and heating, in step S2, at least one C12-C22 fatty alcohol at a concentration of 1-5% by weight of the foamable skin composition and at least one ester and/or vegetable oil at a concentration of 1-40% by weight of the foamable skin composition, at least one pre-warmed non-ionic surfactant at a concentration of 1-15% by weight of the foamable skin composition, and at least one emollient at a concentration of 0.5-10% by weight of the foamable skin composition to form an oil mixture. The method further comprises mixing and optionally homogenizing, in step S3, the water mixture and the oil mixture. The method additionally comprises optionally adjusting, in step S4, the pH of the foamable skin composition to achieve an acidic pH. The foamable skin composition produced according to the above presented method has an acidic pH.

In an embodiment, the method described above is used to produce a foamable skin composition according to any of the embodiments.

The adjustment of the pH of the foamable skin composition in step S4 is optional since the foamable skin composition may, following the mixing and optionally homogenizing the water mixture and the oil mixture, already have an acidic pH. In such a case, no additional pH adjustment is needed, but may of course be performed if the resulting pH following the mixing and optionally homogenizing the water mixture and the oil mixture is different from a target acidic pH of the resulting foamable skin composition.

In an embodiment, the method comprises adding at least one pH adjuster at a concentration sufficient to achieve an acidic pH of the foamable skin composition. Thus, in this embodiment, at least one pH adjuster is added to adjust the pH of the foamable skin composition. The at least one pH adjuster could be added to the water mixture, to the oil mixture and/or to the mixture of the water and oil mixtures.

Steps S1 and S2 in FIG. 1 can be performed serially in any order, i.e., step S1 followed by step S2 or step S2 followed by step S1, or at least partly in parallel.

In an embodiment, step S1 comprises mixing and heating water, at least one humectant at a concentration of 1-40% by weight of the foamable skin composition and the at least one C12-C22 fatty acid at a concentration of 1-3% by weight of the foamable skin composition until the at least one C12-C22 fatty acid melts to form the water mixture.

In a particular embodiment, step S1 comprises mixing water and the at least one humectant. The mixed water and at least one humectant is then heated to 70-85° C., preferably about 75° C. The at least one C12-C22 fatty acid is added to the heated mixture and mixed until the at least one C12-C22 fatty acid melts to form the water mixture.

In an embodiment, step S2 comprises mixing the at least one C12-C22 fatty alcohol at a concentration of 1-5% by weight of the foamable skin composition and the at least one ester and/or vegetable oil at a concentration of 1-40% by weight of the foamable skin composition. The at least one pre-warmed non-ionic surfactant is then added at a concentration of 1-15% by weight of the foamable skin composition.

The at least one emollient is added at a concentration of 0.5-5% by weight of the foamable skin composition to form the oil mixture. Finally, the oil mixture is heated to 70-85° C., preferably 75° C.

In a preferred embodiment, the water mixture and the oil mixture thereby preferably have substantially the same temperature when mixing the two mixtures in step S3.

In an embodiment, step S3 comprises mixing the water mixture and the oil mixture and homogenizing the water mixture and the oil mixture for at least 5 minutes, preferably 10 to 15 minutes, to form a homogenized mixture. The homogenized mixture is then cooled to 15-30° C., such as to room temperature.

EXAMPLES

Example 1

A foamable skin composition, denoted Pro Q derm herein, according to the present invention was manufactured. The composition provided a stable foam for skin care with a low pH and skin friendly ingredients. The composition also had a low viscosity and was easy to fill in a production line while providing a rich foam texture.

Ingredients (% by Weight of the Foamable Skin Composition)

| | |
|---|---|
| Water | 76.5% |
| Stearic acid, palmitic acid (1:1) | 2.0% |
| Propanediol | 5.0% |
| Diisopropyl adipate | 2.5% |
| Carpylic/capric triglyceride | 2.5% |
| Butylene glycol dicaprylate/dicaprate | 2.0% |
| Cetearyl alcohol | 2.0% |
| Sorbitan laurate | 2.0% |
| Polyglycerol-4 laurate/succinate | 2.9% |
| Squalane | 2.0% |
| Allantoin | 0.5% |
| Tocopherol | 0.1% |
| Lactic acid | Adjust pH |

Mixing Instruction

Water Phase

Mix water with propanediol. Heat the mixture to 75° C. Add the fatty acids, stearic acid and palmitic acid mixture, and mix until all fatty acids have melted.

Oil Phase

Mix diisopropyl adipate, caprylic/capric triglyceride, butylene glycol dicaprylate/dicaprate and cetearyl alcohol. Add pre-warmed (40° C.) sorbitan laurate and polyglycerol-4 laurate/succinate one by one. Add squalene and heat the mixture to 75° C.

Add the oil phase to the water phase and mix. Homogenize for 10-15 min. Cool down to 30° C. and adjust to wanted pH with lactic acid.

Example 2

A foamable skin composition according to the present invention was manufactured. The composition provided a stable foam for skin care with a low pH and skin friendly ingredients. The composition also had a low viscosity and was easy to fill in a production line while providing a rich foam texture.

Ingredients (% by Weight of the Foamable Skin Composition)

| | |
|---|---|
| Water | 67.2% |
| Stearic acid, palmitic acid (1:1) | 2.0% |
| Propanediol | 4.0% |
| Diisopropyl adipate | 2.5% |
| Carpylic/capric triglyceride | 2.5% |
| Butylene glycol dicaprylate/dicaprate | 2.0% |
| Cetearyl alcohol | 2.0% |
| Sorbitan laurate | 2.0% |
| Polyglycerol-4 laurate/succinate | 2.9% |
| Squalane | 2.0% |
| Allantoin | 0.5% |
| Tocopherol | 0.4% |
| Urea | 10% |
| Lactic acid | Adjust pH |

The foamable skin composition was manufactured according to the mixing instructions in Example 1 but with the addition of urea just prior to the homogenization.

Example 3

The Pro Q derm composition according to Example 1 was compared to three skin foam formulations available on the market: SALVAX® foam by Exeltis USA Dermatology, Inc., Egg mousse body oil by Too Cool For School and AriPro Hydrating Barrier Mousse by Pharmacy2U.

SALVAX® foam is a skin mousse with low pH for treatment of various skin conditions. Ingredients: salicylic acid (6%), dimethicone, ethylparaben, glycerin, methylcellulose, methylparaben, phenoxyethanol, polyoxyl 40 stearate, polysorbate 20, polysorbate 80, povidone, propylene glycol, propylparaben, purified water, sodium citrate, sodium hydroxide, stearic acid, and trolamine. Isobutane and propane as propellants.

Egg mousse body oil is a hydrating body mousse with higher pH. Ingredients: Water, Mineral Oil, Tetrafluoropropene, Butylene Glycol, Cyclopentasiloxane, Caprylic/Capric Triglyceride, Stearic Acid, Glycerin, Trehalose, Pentylene Glycol, *Butyrospermum Parkii* (Shea) Butter, Egg Yolk Extract, Albumen Extract, *Prunus Amygdalus Dulcis* (Sweet Almond) Oil, *Persea Gratissima* (Avocado) Oil, *Olea Europaea* (Olive) Fruit Oil, *Simmondsia Chinensis* (Jojoba) Seed Oil, *Sclerocarya Birrea* Seed Oil, Honey Extract, Milk Protein Extract, Polysorbate 60, Triethanolamine, Dimethicone, Glyceryl Stearate, Sorbitan Sesquioleate, Caprylyl Glycol, Peg-100 Stearate, Acrylates/C10-30 Alkyl Acrylate Crosspolymer, Cetearyl Alcohol, Xanthan Gum, Disodium EDTA, Phenoxyethanol, Methylparaben, Fragrance.

AriPro is a skin mousse with higher pH for treatment of various skin conditions. Ingredients: Purified water, Propylene glycol, Palmitic acid, Stearic acid, PVP, Glycerin, Polysorbate 20, Triethanolamine, and Dimethicone. Butane, propane and isobutane as propellant.

Pro Q derm according to Example 1 used butane, isobutane and propane as propellant.

Egg mousse body oil and AriPro was selected as stable skin foams available on the market. These stable skin foams, however, have alkaline pH values. SALVAX® foam is a skin mousse with an acidic pH and light texture.

Table 1 below lists the pH values of the four tested compositions.

TABLE 1 pH of compositions

| Composition | pH |
|---|---|
| Pro Q derm | 4.40 |
| SALVAX ® foam | 4.50 |
| Egg mousse body oil | 7.85 |
| AriPro | 8.50 |

Foam stability of the four foams were compared according to the following protocol.

1. The cap of the container was removed.
2. The container was shaken for 3-5 seconds.
3. The valve was actuated to dispense foam onto a flat metallic tray very close to a ruler at an initial height of 3-6 cm. Directly after dispensing the foam, the initial height of the foam was measured (Height initial) and a timer (1 min) was started.
4. The height was measured again after 1 min (Height after 1 min).
5. The decrease of the foam height was calculated as ((Height initial−Height after 1 min)/Height initial)×100.
6. The foam stability was defined as 100% minus the decrease of the foam height.

FIG. 2 illustrates the foam stability of the four tested foams. SALVAX® foam had 0% foam stability after 1 min and no foam was left. Pro Q derm had a pH value similar to SALVAX® foam but had a significantly higher foam stability after 1 min. In fact, the foam stability of Pro Q derm was almost as high as the foam stability of Egg mousse body oil and AriPro although Pro Q derm had an acidic pH of 4.40, whereas Egg mousse body oil and AriPro had alkaline pH of 7.85 and 8.50, respectively.

Figure 3:
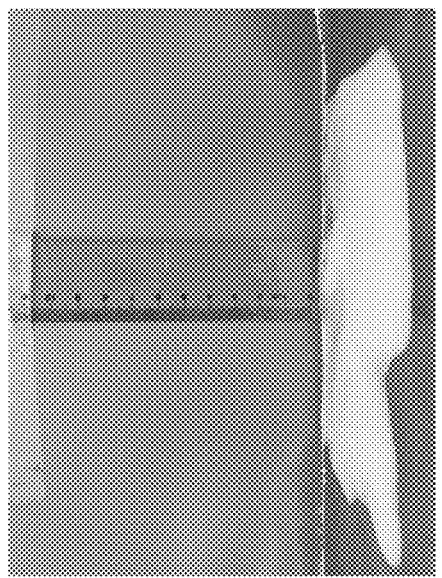
FIG. 3 is a photograph of a SALVAX® foam 1 min after dispensing.

FIGS. 3 and 4 are photographs of the foam 1 min after dispensing for SALVAX® foam in FIG. 3 and for Pro Q derm in FIG. 4.

The foamable skin composition of the present invention thereby provides a stable foam even at an acidic pH.

Example 4

A foamable skin composition according to the present invention was manufactured. The composition provided a stable foam for skin care with a low pH and skin friendly ingredients. The composition also had a low viscosity and was easy to fill in a production line while providing a rich foam texture.

Ingredients (% by Weight of the Foamable Skin Composition)

| | |
|---|---|
| Water | 52.2% |
| Stearic acid, palmitic acid (1:1) | 2.0% |
| Propanediol | 4.0% |
| Diisopropyl adipate | 2.5% |
| Carpylic/capric triglyceride | 2.5% |
| Butylene glycol dicaprylate/dicaprate | 2.0% |
| Cetearyl alcohol | 2.0% |
| Sorbitan laurate | 2.0% |
| Polyglycerol-4 laurate/succinate | 2.9% |
| Squalane | 2.0% |
| Allantoin | 0.5% |
| Tocopherol | 0.4% |
| Urea | 25% |
| Lactic acid | Adjust pH |

The foamable skin composition was manufactured according to the mixing instructions in Example 1 but with the addition of urea just prior to the homogenization.

Example 5

Foam stability of three foamable skin compositions according to the invention was measured using the protocol outlined in Example 3.

The results of the foam stability measurements of three foamable skin compositions are presented in Table 2. The foamable skin compositions were the foamable skin composition according to Example 1, the foamable skin composition according to Example 4 and a foamable skin composition based on Example 1 and comprising a sun filter with sun protection factor (SPF) of 50.

TABLE 2

| foam stability | | |
|---|---|---|
| Composition | pH | Foam stability (%) |
| Example 1 | 4.4 | 92.1 |
| Example 4 | 5.2 | 89 |
| Example 1 + SPF 50 sun filter | 4.6 | 84 |

The foamable skin compositions of the invention had very high foam stability even at acidic pH. The foam stability furthermore remained very high even when adding urea (compare Example 1 and Example 4) or adding SPF 50 sun filter (compare Example 1 and Example 1+SPF 50 sun filter).

Example 6

Foam density of three foamable skin compositions according to the invention was measured using the following protocol.

1. A weighing cap where the volume already has been determined was use.
2. The weighing cap was weighed. The balance was tared.
3. The cap of the container was removed.
4. The container was shaken for 4 seconds.
5. The valve was actuated to dispense foam into the weighing cap. The cap was completely filled with foam and no large cavities were created.
6. Excessive foam was removed after 30 s with a spatula.
7. The weighing cap plus foam was weighed. The weight was with 2 decimals.
8. The weighing cap was rinsed with water and then dried completely with a paper towel.
9. The procedure was repeated at least three times.
10. The foam density was calculated for each weighing session according to the following equation: $\rho = m/V$, wherein m represents the weight (mg) of the foam, V represents the volume of the cap (ml) and $\rho$ is the density of the foamable skin composition (mg/ml).
11. The average foam density for the tested foamable skin composition was calculated and reported in mg/ml with no decimals.

The results of the density measurements of the three foamable skin compositions tested in Example 5 are presented in Table 3.

TABLE 3

| foam density | | |
|---|---|---|
| Composition | pH | Foam density (mg/ml) |
| Example 1 | 4.4 | 31 ± 0.8 |
| Example 4 | 5.2 | 30 ± 0.6 |
| Example 1 + SPF 50 sun filter | 4.6 | 33 ± 1.3 |

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A foamable skin composition comprising:
   at least one C12-C22 fatty acid at a concentration of 1-3% by weight of said foamable skin composition;
   at least one C12-C22 fatty alcohol at a concentration of 1-5% by weight of said foamable skin composition;
   at least one ester at a concentration of 1-40% by weight of said foamable skin composition, wherein said at least one ester is a mixture of caprylic triglyceride, capric triglyceride, diisopropyl adipate, butylene glycol dicaprylate and butylene glycol dicaprate;
   at least one non-ionic surfactant at a concentration of 1-15% by weight of said foamable skin composition;
   at least one emollient at a concentration of 0.5-10% by weight of said foamable skin composition; and
   water, wherein said foamable skin composition has an acidic pH.

2. The foamable skin composition according to claim 1, further comprising at least one propellant.

3. The foamable skin composition according to claim 1, wherein
said at least one C12-C22 fatty acid is at least one C12-C18 fatty acid; and
said at least one C12-C22 fatty alcohol is a C12-C18 fatty alcohol.

4. The foamable skin composition according to claim 3, wherein
said at least one C12-C18 fatty acid is selected from the group consisting of lauric acid, myristic acid, palmitic acid, stearic acid, myristoleic acid, palmitoleic acid, sapienic acid, oleic acid, elaidic acid, vaccenic acid, linoleic acid, linoelaidic acid and a mixture thereof; and
said at least one C12-C18 fatty alcohol is selected from the group consisting of cetearyl alcohol, cetyl alcohol, myristyl alcohol, stearyl alcohol and a mixture thereof.

5. The foamable skin composition according to claim 1, wherein said at least one C12-C22 fatty acid is at a concentration of 1.5-2.5% by weight of said foamable skin composition.

6. The foamable skin composition according to claim 1, wherein said at least one C12-C22 fatty alcohol is at a concentration of 1-4% by weight of said foamable skin composition.

7. The foamable skin composition according to claim 1, wherein said at least one non-ionic surfactant is selected from the group consisting of sorbitan laurate, polyglycerol-4 laurate, polyglycerol-4 succinate, polysorbate and a mixture thereof.

8. The foamable skin composition according to claim 1, wherein said at least one non-ionic surfactant is at a concentration of 2-8% by weight of said foamable skin composition.

9. The foamable skin composition according to claim 1, further comprising at least one vegetable oil at a concentration of 1-40% by weight of said foamable skin composition.

10. The foamable skin composition according to claim 9, wherein said at least one vegetable oil is selected from the group consisting of sesame oil, olive oil, almond oil, apricot kernel oil, avocado oil, evening primrose oil, grapeseed oil, hazelnut oil, jojoba oil, pumpkin oil, rosehip oil, safflower oil, walnut oil, wheatgerm oil, sunflower oil, and a mixture thereof.

11. The foamable skin composition according to claim 1, wherein said at least one ester is at a concentration of 1-20% by weight of said foamable skin composition.

12. The foamable skin composition according to claim 1, wherein said at least one emollient is selected from the group consisting of squalane, isodecyl neopentanoate, dimethicone, paraffinum liquidum, diethylhexyl maleate, diethylhexyl malate and a mixture thereof.

13. The foamable skin composition according to claim 1, wherein said at least one emollient is at a concentration of 1-8% by weight of said foamable skin composition.

14. The foamable skin composition according to claim 1, further comprising at least one humectant at a concentration of 1-40% by weight of said foamable skin composition.

15. The foamable skin composition according to claim 14, wherein said at least one humectant is selected from the group consisting of 1,3-propanediol, glycerol, urea, betaine and a mixture thereof.

16. The foamable skin composition according to claim 14, wherein said at least one humectant is at a concentration of 1-30% by weight of said foamable skin composition.

17. The foamable skin composition according to claim 1, further comprising at least one pH adjuster at a concentration sufficient to achieve an acidic pH of said foamable skin composition.

18. The foamable skin composition according to claim 1, wherein said foamable skin composition has a pH of 3-6.

19. The foamable skin composition according to claim 1, wherein said foamable skin composition has a foam density of at least 50%, wherein said foam density is defined as $100 \times H_1/H_0\%$, $H_0$ represents height of a foam directly after dispensing said foamable skin composition to form said foam and $H_0$ represents height of said foam 1 minute after dispensing said foamable skin composition.

20. The foamable skin composition according to claim 1, wherein a foam formed by dispensing said foamable skin composition has a density within an interval of from 20 mg/ml up to 60 mg/ml.

21. A foamable skin composition, comprising:
a mixture of stearic acid and palmitic at a concentration of 1-3% by weight of said foamable skin composition;
cetearyl alcohol at a concentration of 1-5% by weight of said foamable skin composition;
a mixture of caprylic triglyceride, capric triglyceride, diisopropyl adipate, butylene glycol diaprylate and butylene glycol dicaprate at a concentration of 1-40% by weight of said foamable skin composition;
a mixture of sorbitan laurate, polyglycerol-4 laurate and polyglycerol-4 succinate at a concentration of 1-15% by weight of said foamable skin composition;
squalene at a concentration of 0.5-5% by weight of said foamable skin composition; and
water, wherein said foamable skin composition has an acidic pH.

22. The foamable skin composition according to claim 21, comprising:
said mixture of stearic acid and palmitic acid at a concentration of 2% by weight of said foamable skin composition;
cetearyl alcohol at a concentration of 2% by weight of said foamable skin composition;
diisopropyl adipate at a concentration of 2.5% by weight of said foamable skin composition;
a mixture of caprylic triglyceride and capric triglyceride at a concentration of 2.5% by weight of said foamable skin composition;
a mixture of butylene glycol dicaprylate and butylene glycol dicaprate at a concentration of 2% by weight of said foamable skin composition;
1,3-propanediol at a concentration of 4 or 5% by weight of said foamable skin composition;
sorbitan laurate at a concentration of 2% by weight of said foamable skin composition;
a mixture of polyglycerol-4 laurate and polyglycerol-4 succinate at a concentration of 2.9% by weight of said foamable skin composition;
squalane at a concentration of 2% by weight of said foamable skin composition; and
water.

23. A method of producing a foamable skin composition according to claim 1, said method comprising:
a) mixing and heating water and at least one C12-C22 fatty acid at a concentration of 1-3% by weight of said foamable skin composition until said at least one C12-C22 fatty acid melts to form a water mixture;
b) mixing and heating at least one C12-C22 fatty alcohol at a concentration of 1-5% by weight of said foamable skin composition and at least one ester at a concentration of 1-40% by weight of said foamable skin composition, at least one pre-warmed non-ionic surfactant at a concentration of 1-15% by weight of said foamable skin composition, and at least one emollient at a concentration of 0.5-10% by weight of said foamable skin composition to form an oil mixture;

c) mixing said water mixture and said oil mixture; and d) optionally adjusting the pH of said foamable skin composition to achieve an acidic pH, wherein said foamable skin composition has an acidic pH and wherein said at least one ester is a mixture of caprylic triglyceride, capric triglyceride, diisopropyl adipate, butylene glycol dicaprylate and butylene glycol dicaprate.

* * * * *

UNITED STATES PATENT AND TRADEMARK OFFICE
CERTIFICATE OF CORRECTION

| | | |
|---|---|---|
| PATENT NO. | : 10,869,818 B2 | Page 1 of 1 |
| APPLICATION NO. | : 16/185535 | |
| DATED | : December 22, 2020 | |
| INVENTOR(S) | : Marie Hedrén et al. | |

It is certified that error appears in the above-identified patent and that said Letters Patent is hereby corrected as shown below:

On the Title Page

Item (30), change "1751397" to --1751397-9--.

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*